United States Patent [19]

Malpass et al.

[11] Patent Number: 5,777,143
[45] Date of Patent: Jul. 7, 1998

[54] HYDROCARBON SOLUBLE ALKYLALUMINOXANE COMPOSITIONS FORMED BY USE OF NON-HYDROLYTIC MEANS

[75] Inventors: Dennis B. Malpass. La Porte, Tex.; Stanley W. Palmaka, Yonkers, N.Y.; Gregory M. Smith, Bethel, Conn.; Jonathan S. Rogers, Rochester, N.Y.

[73] Assignee: Akzo Nobel NV. Arnhem, Netherlands

[21] Appl. No.: 736,075

[22] Filed: Oct. 25, 1996

Related U.S. Application Data

[63] Continuation-in-part of Ser. No. 576,892, Dec. 22, 1995, and a continuation-in-part of Ser. No. 651,290, May 22, 1996, Pat. No. 5,728,855.

[51] Int. Cl.$^6$ .................. C07F 5/06; B01J 31/06
[52] U.S. Cl. .................. 556/179; 556/180; 556/187; 502/103; 502/117; 502/152; 526/160; 526/943
[58] Field of Search .................. 556/179, 180, 556/187; 502/103, 117, 152; 526/160, 943

[56] References Cited

U.S. PATENT DOCUMENTS 5,066,631 11/1991 Sangokoya et al. .................. 502/152
5,480,848 1/1996 Geerts .................. 502/103

*Primary Examiner*—Porfirio Nazario-Gonzalez
*Attorney, Agent, or Firm*—Richard P. Fennelly; Louis A. Morris

[57] ABSTRACT

A hydrocarbon-soluble alkylaluminoxane composition, such as, methylaluminoxane or even a modified methylaluminoxane, can be prepared by preparing an alkylaluminoxane precursor via non-hydrolytic means, such as, by treating at least one trialkylaluminum compound with a compound containing an oxygen-carbon bond, adding to that precursor an effective amount of an organoaluminum compound which prevents formation of insoluble species, such as, a trialkylaluminum compound where each alkyl group contains two or more carbon atoms, and converting that modified precursor to an alkylaluminoxane, such as, by thermolysis. In a distinct embodiment of the invention, if an insoluble methylaluminoxane product is formed using the non-hydrolytic technique, it can be solubilized by treatment with a solubilizing amount of an alkylaluminoxane, prepared by either hydrolytic or non-hydrolytic means, wherein the alkyl moieties contain two or more carbon atoms. These aluminoxane products show high solubility in aliphatic hydrocarbons and improved thermal stability in aromatic hydrocarbons.

23 Claims, No Drawings

HYDROCARBON SOLUBLE ALKYLALUMINOXANE COMPOSITIONS FORMED BY USE OF NON-HYDROLYTIC MEANS

This application is a continuation-in-part of U.S. Ser. No. 576,892, now allowed, filed Dec. 22, 1995 and a continuation-in-part of U.S. Ser. No. 651,290, now U.S. Pat. No. 5,728,855, filed May 22, 1996.

BACKGROUND OF THE INVENTION

This invention relates generally to hydrocarbon solvent solutions of alkylaluminoxane compounds. More specifically, it relates to a non-hydrolytic process for preparing stable, aliphatic hydrocarbon soluble solutions of alkylaluminoxane. It also relates to a non-hydrolytic process for preparing aromatic hydrocarbon solutions of alkylaluminoxanes which tolerate exposure to heat without adverse effects. Aluminoxanes are well known as components for olefin polymerization catalysts. Aluminoxane compounds are chemical species that incorporate Al-O-Al moieties. While a wide range of aluminoxane species are known, their exact structures are not precisely known. The following structures (where R is alkyl and X is an integer of from about 1 to about 40) have been depicted:

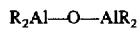

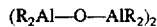

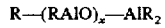

Cyclic and cage cluster structures have also been proposed. Such materials, as would be recognized by the person of ordinary skill in the art are complex mixtures of various species which can easily undergo dynamic exchange reactions and structural rearrangements. A recent review of these materials was authored by S. Pasynkiewicz and appears in Polyhedron, Vol. 9, pp. 429–453 (1990).

Polymethylaluminoxanes (PMAOs), for example, are well known materials with wide utility in olefin polymerization using single-site, or metallocene-based, polymerization catalyst systems (See, for example, Col. 1, lines 14–29 of U.S. Pat. No. 4,960,878 to C. C. Crapo et al.). PROs have been conventionally prepared by controlled hydrolysis of trimethylaluminum (TMAL). Since TMAL is an expensive starting material, the resulting PMAO is expensive. Generally, hydrolysis occurs with some loss of aluminum to insoluble species. Generally, PMAOs also have very low solubility in aliphatic solvents, which limits their utility, as well as poor storage stability for solutions containing them. (See, for example, Col. 1, lines 30–46 of U.S. Pat. No. 4,960,878). Finally, it is generally polymethylaluminoxanes that have been the most useful products of this general class of material: other alkylaluminoxanes do not work as well.

The problems of low yield, poor solubility, poor storage stability, and expensive reagents in preparation of PMAO have previously been attacked, with only limited success, in several ways. One method was to make predominantly PMAO, but include some components from hydrolysis of other aluminum alkyls, to form the so-called "modified methylaluminoxane" (MMAO). This yields predominantly methyl-containing aluminoxanes in improved yields, with improved solution storage stability as well as improved solubility in aliphatic solvents, at lower cost.

U.S. Pat. No. 5,041,584 describes hydrolytic methods of forming aliphatic solvent soluble modified methylaluminoxane compositions, as do U.S. Pat. Nos. 5,157,008; 5,157,1378; and 5,066,631. In particular, U.S. Pat. No. 5,066,631 describes a method for converting a conventional, insoluble polymethylaluminoxane, prepared by hydrolytic means, into a soluble modified methylaluminoxane by using a tri-n-alkylaluminum compound containing at least two carbon atoms in its alkyl moieties.

Copending U.S. Ser. No. 576,892 describes a general non-hydrolytic method of preparing aluminoxanes which departs from the previously described hydrolytic means known to the art.

We have now found a novel non-hydrolytic method to form aliphatic hydrocarbon soluble methylaluminoxane compositions in which aluminum-containing starting materials are converted, without loss of insoluble aluminum-containing materials, or the formation of difficult to handle intermediate compositions comprising slurries of insoluble material, into high activity methylaluminoxane compositions. This method also improves upon the non-hydrolytic method described in U.S. Ser. No. 576,892 by providing a method for preparing aromatic hydrocarbon solutions of alkylaluminoxanes with improved tolerance when exposed to heat.

SUMMARY OF THE INVENTION

The present invention relates to novel processes for forming a hydrocarbon soluble modified methylaluminoxane (MMAO) composition with high polymerization activity. There are several aspects to the present invention.

The first aspect, in general, is the use of a non-hydrolytic method for forming catalytically useful alkylaluminoxanes which is described in general outline in co-pending U.S. Ser. No. 576,892, which is incorporated herein by reference. The non-hydrolytic method comprises two steps: first, an alkylaluminoxane precursor composition is formed via non-hydrolytic means; and, second, this precursor composition is converted, typically by thermolysis, to a catalytically useful alkylaluminoxane composition.

The second aspect of the process of the present invention is the novel incorporation of an organoaluminum compound, wherein the alkyl groups contain two or more carbon atoms, into the previously described non-hydrolytic aluminoxane formation process. The incorporation of this organoaluminum compound can occur either a) before formation of the alkylaluminoxane precursor, b) after formation of the desired alkylaluminoxane precursor, but before conversion to the desired alkylaluminoxane product, or c) after the conversion is complete.

The process of the present invention has several advantages over previously known techniques. First, it allows preparation of alkylaluminoxane compositions, which are soluble in aliphatic hydrocarbons, via the general type of non-hydrolytic route which the copending application has previously described as giving a higher activity product than that available via conventional hydrolytic routes. Second, it allows for preparation of alkylaluminoxane compositions, which are soluble in aliphatic hydrocarbons, without forming intermediate compositions that contain precipitated solids. This simplifies handling and equipment requirements. Third, it allows for the preparation of alkylaluminoxane compositions with near quantitative yields of aluminum values. Fourth, it allows for the preparation of alkylaluminoxane compositions in aromatic hydrocarbon solvents with improved thermal stability and improved activity.

DETAILED DESCRIPTION OF THE INVENTION

As used in this specification (and in the attached claims) The term "alkylaluminoxane composition" is to be construed as covering aluminoxanes which contain "alkyl" moieties, such as the preferred methyl moiety, as essential constituent elements, along with, if desired, "hydrocarbyl" moieties which include such carbon-hydrogen containing groups as alkyl containing two or more carbon atoms, aryl (e.g., phenyl), aryl-substituted alkyl of the foregoing type, alkyl substituted aryl alkenyl, and the like suitable examples of hydrocarbyl groups include those contributed to the composition by such reagents as triethylaluminum, triisobutylaluminum, tri-n-octylaluminum, and tris(2,4,4-trimethylpentyl) aluminum. The term "modified methylaluminoxane" as used herein, in connection with the either the final aluminoxane product or the precursor for making it, is intended to refer to the aluminoxanes containing hydrocarbyl groups other than methyl, particularly those also containing alkyl groups having at least two carbon atoms therein. In the description which follows, the main focus will be on the preferred methylaluminoxane species, but it should be borne in mind that one or more optional hydrocarbyl moieties can be present as well.

The solutions of the invention can be formed by first preparing an alkylaluminoxane precursor by non-hydrolytically reacting trimethylaluminum (TMAL) with an oxygenating agent (a compound containing an oxygen-carbon bond), such as carbon dioxide, in hydrocarbon media, as more fully described in copending U.S. application Ser. No. 576,892, which is incorporated herein in its entirety.

As mentioned in that copending application, the precursor intermediate composition can be formed by using a reagent, containing an oxygen-carbon chemical bond. Suitable reagents which can be used can be selected, for example, from the alcohols, the ketones, and the carboxylic acids as representative examples. A particularly suitable reagent which has been found to work is carbon dioxide.

In a preferred embodiment this precursor composition is formed by treating trimethylaluminum with an oxygenated organic compound such as an alcohol, ketone, carboxylic acid or carbon dioxide. In the case of carboxylic acids or carbon dioxide, some aluminoxane moieties will form (see, for example, copending application U.S. Ser. No. 08/651, 290, filed on May 22, 1996).

In all these cases, as is well known in the art, alkoxyaluminum or arylalkoxyaluminum moieties will be formed. The following equations represent possible, non-limiting, examples of the reactions of trimethylaluminum and oxygenated organic molecules to form alkoxyaluminum or arylalkoxyaluminum-based aluminoxane precursor compositions (R and R' being the same or different and being selected from alkyl and/or aryl and TMAL indicating trimethylaluminum):

 (I)

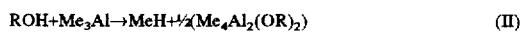 (II)

 (III)

 (IV)

The most preferred embodiment of the present invention is to use a carboxylic acid or carbon dioxide as they form both a methylaluminoxane precursor containing the alkoxyaluminum or arylalkoxyaluminum moieties and the desired methylaluminoxane products.

Once this preferred methylaluminoxane precursor composition is formed, an important component of the present invention is the thermal and/or catalytic transformation of this precursor to form the desired catalytically useful methylaluminoxane composition.

The preferred method for transforming the methylaluminoxane precursor is to optionally add, or form in situ, a catalytically effective amount of methylaluminoxane with the precursor and heat the material at the lowest temperature sufficient to effect conversion to the desired methylaluminoxane composition in a reasonable amount of time.

The present invention, in its most preferred embodiment is a novel process, for forming catalytically useful polymethylaluminoxane with the resulting, polymethylaluminoxane composition, in certain embodiments being a novel polymethylaluminoxane composition which is substantially free of trimethylaluminum. This process comprises the thermal and/or catalytic transformation of an appropriately constituted precursor composition as earlier described. A preferred method for preparing the precursor composition is treatment of trimethylaluminum with a carboxylic acid or with carbon dioxide. However, as will be appreciated by a person of ordinary skill in the art, there are many other methods which can be used to prepare the precursor composition which is transformed into the desired final product.

As will be appreciated, the processes of the present invention can be conducted in the presence of a suitable hydrocarbon solvent or in the absence of such solvent.

If desired, supported polyalkylaluminoxane compositions can be prepared by conducting the aforementioned reaction in the presence of a suitable support material. Alternatively, supported alkylaluminoxanes may also be prepared by forming the alkylaluminoxanes of this invention in a discrete, separate step and subsequently allowing the alkylaluminoxane to react with the support material. Oxidic support materials, such as silica, are especially preferred.

As will be appreciated by the person of ordinary skill in the art, the aluminoxane products that can be made by the process of the present invention are useful as cocatalysts, for example, in those single-site (metallocene-based) catalyst systems which are useful in the polymerization of olefin monomers in a manner analogous to that in current use with the aluminoxane compositions that are currently known and used in that manner.

As earlier indicated, at some point during the preparation of the precursor composition, or during the process of forming the catalytically active polyalkylaluminoxane compositions, an effective amount of an organoaluminum compound (e.g., a trialkylaluminum) compound is added. There compounds may be added before, during, or after conversion of the precursor to alkylaluminoxane. A preferred range for the amount to add is from about 0.1% mole % to about 50 mole %, most preferably from about 1 mole % to about 20 mole %. Thermolysis is performed by mixing and heating at temperatures sufficient to convert the precursor to an alkylaluminoxane. There is no formation of insoluble species when the present invention is practiced. Examples 1 through 7, which follow, illustrate the advantages obtained by use of the present invention. Note that these Examples match the performance obtained in Example 9, yet circumvent the need to handle a slurry.

Another method of obtaining a hydrocarbon soluble MMAO composition is by non-hydrolytically reacting trimethylaluminum (TMAL), with an oxygenating agent, for example, carbon dioxide, in the presence of a trialkylaluminum compound or alkylaluminoxane followed by conversion of the resulting alkylaluminoxane precursor to an alkylaluminoxane via thermolysis. This is illustrated in Examples 6, and 7.

A final method of obtaining a hydrocarbon soluble MMAO composition is by using an amount of an alkylaluminoxane composition containing alkylaluminum groups with 2 or more carbon atoms to solubilize an aliphatic solvent slurry of a non-hydrolytically prepared methylaluminoxane. as illustrated in Example 8 and as taught for conventional hydrolytically formed methylaluminoxane compositions in U.S. Pat. No. 5,066,631 to S.A. Sangokoya et al.

The present invention allows for more soluble aluminoxanes in aliphatic hydrocarbon solvent and more heat resistant aluminoxanes in aromatic hydrocarbon solvent.

The Examples which follow further illustrate certain embodiments of the present invention as well as the advantages one obtains from its use.

PROCEDURES USED IN EXAMPLES

Standard air-free glove box and Schlenk line techniques were used in these examples. Samples of neat trimethylaluminum (TMAL, 37.4 wt. % Al), neat tri-n-octylaluminum (TNOAL, 6.6 wt. % Al), neat triisobutylaluminum (TIBAL, 13.4 wt. % Al) and n-octylaluminoxane (NOA, 2.1 wt. % Al in ISOPAR-E solvent, a mixed $C_8$ aliphatic hydrocarbon, 0.8 oxygen:aluminum) were obtained from Akzo Nobel Chemicals Inc. and used as received. ISOPAR-E solvent was obtained from Exxon and was dried over 4A molecular sieves prior to use. The $CO_2$ was obtained from Matheson (Coleman Instrument grade) and was also used as received.

Ethylene polymerization tests were conducted in hexane at 85° C. under a total pressure of 150 psig using rac-ethylenebis-indenylzirconium dichloride:trimethylaluminum (1:30) as the catalyst precursor component with the aluminoxane (or alkoxy aluminum precursor) being present at 1000/1 Al:Zr. The polymerization tests were run for a forty-five minute period. Afterward, the polymer was recovered by filtration, was dried and was weighed.

EXAMPLE 1

This Example illustrates the formation of a precursor composition for subsequent use.

Inside a nitrogen-filled glovebox, 79.92 grams of neat trimethylaluminum (TMAL) and 56.93 grams of ISOPAR-E solvent was added to a 500 mL Andrews Glass glass pressure reaction vessel equipped with a multi-ported stirrer head. The TMAL/ISOPAR-E solvent solution was treated with 19.3 grams of $CO_2$, over a nine hour period at 20° C. to 50° C., to prepare PRECURSOR A with an oxygen/aluminum (O/Al) ratio of 0.79. PRECURSOR A, a clear, colorless, mobile solution, contained 18.7 wt % aluminum and showed relatively low activity in an ethylene polymerization test (150 kgPE/gZr—hr).

EXAMPLES 2 and 2A

These Examples illustrate that a product is obtained which is not fully soluble in aliphatic solvent if an organoaluminum compound is not added to the system in order to achieve full solubilization.

Inside a nitrogen-filled glovebox, 40.97 grams PRECURSOR A was mixed with 18.12 grams of ISOPAR-E solvent, inside a 130 mL vial, to make a solution at 13 wt. % Al. This sample was stirred and heated in a 120° C. oil bath. After eighteen hours, the sample began to turn hazy and eventually turbid. During thermolysis, 3.50 grams of gas (primarily neopentane) was evolved from the sample. The $^1H$ NMR spectra were consistent with the formation of aluminoxane. This finely suspended slurry contained 13.9 wt % Al and showed an activity of 1400 kg PE/g Zr—hr in an ethylene polymerization test. After the slurry was allowed to stand, the supernatant contained 11.8 wt % Al.

In a similar experiment, a similar suspension of finely divided particles was prepared. Both the slurry and the supernatant, obtained after allowing the suspended particles to settle out, were evaluated in a polymerization test. The slurry contained 13.7 wt % Al and, in an ethylene polymerization test, showed an activity of 1300 kg PE/g Zr—hr. The clear and colorless supernatant solution contained 12.9 wt % Al and showed an activity of 1200 kg PE/g Zr—hr in an ethylene polymerization test.

EXAMPLE 3

Inside a nitrogen-filled glovebox, 6.00 grams of PRECURSOR A, 1.71 grams of neat tri-n-octylaluminum (TNOAL), and 1.76 grams of ISOPAR-E solvent were charged to a 30 mL reaction vial. The contents were stirred and heated for twenty-three hours at 120° C. During this period, the sample lost 0.31 grams as evolved gas and remained clear. This sample had an aluminum content of 13.6 wt % and an activity of 1400 kgPE/gZr—hr in an ethylene polymerization test.

EXAMPLE 4

Inside a nitrogen-filled glovebox, 6.00 grams of PRECURSOR A, 0.84 grams of triisobutylaluminum (TIBAL) and 2.64 grams of ISOPAR-E solvent were charged to a 30 mL reaction vial. The contents were stirred and heated for twenty-three hours at 120° C. During this period, 0.33 grams were lost as evolved gas. The sample remained clear and soluble. This sample had an aluminum content of 13.8 wt % and an activity of 780 kgPE/gZr—hr in an ethylene polymerization test.

EXAMPLE 5

Inside a nitrogen-filled glovebox, 10.00 grams of PRECURSOR A, and 17.73 grams of n-octylaluminoxane (NOA) were charged into a 130 mL reaction vial. The contents were stirred and heated for twenty-three hours at 120° C. During this period, the sample remained clear with 0.10 gram mass loss due to evolved gas. The resultant solution had an aluminum content of 8.1 wt % Al and an activity of 550 kgPE/gZr—hr in an ethylene polymerization test.

EXAMPLE 6

Inside a nitrogen-filled glovebox, 5.00 grams of neat trimethylaluminum (TMAL), 2.85 grams of neat TNOAL, and 6.62 grams ISOPAR-E solvent were charged into a 50 mL reaction vial. With moderate stirring at 25° C., 1.37 grams of $CO_2$ were then charged into the vial to obtain an overall oxygen:aluminum ratio of 0.8. Following the $CO_2$ addition, the sample remained soluble and was heated for twenty-three hours at 120° C. During this period, 0.34 gram was lost as evolved gas. The sample remained clear. Analysis of the solution showed 13.3 wt % aluminum and an activity of 1000 kgPE/gZr—hr in the ethylene polymerization test.

EXAMPLE 7

Inside a nitrogen-filled glovebox, 5.00 grams of neat trimethylaluminum (TMAL), 1.40 grams of neat triisobutylaluminum (TIBAL), and 8.00 grams ISOPAR-E solvent were charged into a 50 mL reaction vial. With moderate stirring at 25° C., 1.33 grams of $CO_2$ was then charged to obtain an overall oxygen:aluminum ratio of about 0.8. Following the $CO_2$ addition, the sample remained soluble and was heated for twenty-three hours at 120° C. During this period, 1.11 grams were lost as evolved gas. The clear solution contained 13.7 wt % aluminum and showed an activity of 860 kgPE/gZr—hr in an ethylene polymerization test.

EXAMPLE 8

Inside a nitrogen-filled glovebox, 5.00 grams of the preformed aluminoxane slurry, prepared in Example 2, and 6.55 grams of n-octylaluminoxane (NOA) were charged into a 30 mL reaction vial. After stirring for twenty-four hours at approximately 25° C., the initially turbid mixture turned clear. The resultant clear, colorless solution had an aluminum content of 7.0 wt % and an activity of 1500 kgPE/gZr—hr in an ethylene polymerization test.

EXAMPLE 9

Inside a nitrogen-filled glovebox, 5.00 grams of the preformed aluminoxane slurry, prepared in Example 2, and 1.06 grams of neat tri-n-octylaluminum (TNOAL) were charged into a 30 mL reaction vial. After stirring for twenty hours at 25° C., the initially turbid mixture became a clear solution. An analysis of the resultant solution showed the aluminum content to be 12.5 weight % and an activity of 1600 kgPE/gZr—hr in an ethylene polymerization test.

EXAMPLE 10

Inside a nitrogen-filled glovebox, 5.00 grams of the preformed aluminoxane slurry, prepared in Example 2, 0.52 gram of neat triisobutylaluminum (TIBAL) and 0.58 gram of ISOPAR-E solvent, were charged into a 30 mL reaction vial. After stirring for twenty hours at 25° C., the initially turbid mixture turned clear. The resultant solution contained 12.5 wt % aluminum and had an activity of 1300 kgPE/gZr—hr in an ethylene polymerization test.

DATA SUMMARY:

| Designation | Weight % Al | Appearance | Activity (kgPE/gZr-hr) |
|---|---|---|---|
| Example 1* | 18.7 | soluble | 150 |
| Example 2 | 13.9 | slurry | 1400 |
| Example 3 | 13.6 | soluble | 1400 |
| Example 4 | 13.8 | soluble | 780 |
| Example 5 | 8.1 | soluble | 550 |
| Example 6 | 13.3 | soluble | 1000 |
| Example 7 | 13.7 | soluble | 860 |
| Example 8 | 7.0 | soluble | 1500 |
| Example 9 | 12.5 | soluble | 1600 |
| Example 10 | 12.5 | soluble | 1300 |

*Example 1 illustrates the preparation of "PRECURSOR A".

The following Examples illustrate how the process of this invention can be applied to aromatic hydrocarbon solutions of alkylaluminoxanes to improve the heat resistance of those solutions. Attempts to evaluate this material in the same manner as in the other Examples resulted in very high, difficult to control, polymerization rates. Using the best control of temperature and other reaction parameters permitted by the experimental apparatus, the activities reported in Examples 11-13 were obtained.

EXAMPLE 11

PMAO was prepared in toluene in a non-hydrolytic process according to the teachings of copending U.S. Ser. No. 576,592. A 12.3 g sample of this PMAO (13.3 wt % Al, 1.63 g contained Al) was placed in a capped and sealed 30 mL serum bottle, was stirred, and was heated to 110° C. for two hours. Though still clear and mobile at 110° C., after cooling to room temperature, this sample was a viscous translucent material with an appearance similar to petroleum jelly. The sample was reheated to 60° C. and was treated with 2.43 g of neat tri-n-octylaluminum (6.6 wt % Al, 0.16 g contained Al). The resulting solution was clear and mobile, both while hot and after cooling. A polymerization test gave 3500 kg PE/g Zr hr.

EXAMPLE 12

PMAO in toluene was prepared in a non-hydrolytic process as described in Example 11. An 11.94 g sample of this PMAO (13.3 wt % Al, 1.59 g contained Al) was placed in a capped and sealed 30 mL serum bottle, along with 0.25 g of neat tri-n-octylaluminum (TNOAL, 6.6 wt % Al, 0.017 g contained Al). The resulting mixture was stirred with heating at 110° C. for two hours. The resulting composition remained clear and mobile, both while hot and after cooling. A polymerization test gave 3200 kg PE/g Zr hr.

EXAMPLE 13

A toluene solution of a methylaluminoxane precursor composition was prepared according to the teachings of copending U.S. Ser. No. 576,892. This precursor contained 13.0 wt % aluminum and had been prepared with 0.4 $CO_2$/Al. A sample of this precursor (100 g, 13.0 wt % Al, 13.0 g contained Al) was treated with neat TNOAL (3.52 g, 7.4 wt % Al, 0.26 g contained Al) and thermolyzed at 110° C. for eighteen hours to prepare a methylaluminoxane composition in quantitative yield. This product contained 13.8 wt % Al and was clear and mobile. A polymerization test gave 3300 kg PE/g Zr hr. The product was thermolyzed at 110° C. for an additional four hours (twenty-two hours total thermolysis time). The resulting product contained 14.3 wt % Al and remained clear and mobile. A polymerization test gave 7600 kg PE/g Zr hr.

COMPARATIVE EXAMPLE 14

A sample of PMAO in toluene was prepared in non-hydrolytic fashion, as in Example 13, with the TNOAL omitted. After eighteen hours thermolysis at 110° C., the sample was clear and mobile. After an additional four hours of thermolysis (twenty-two hours total) at 110° C., the product was an immobile gel, with an appearance similar to petroleum jelly. The sample could not be tested in polymerization because it could not be used to prepare a more dilute solution.

The foregoing Examples, since they are presented merely for illustrative purposes, should not be used in a limiting fashion in construing the present invention. The scope of protection sought is set forth in the claims which follow.

We claim:

1. A process for making a hydrocarbon-soluble alkylaluminoxane composition which comprises:

(a) preparing an alkylaluminoxane precursor via non-hydrolytic means;

(b) adding to that precursor an effective amount of an organoaluminum compound which prevents formation of insoluble species; and (c) converting that modified precursor to an alkylaluminoxane.

2. The process according to claim 1 where the organoaluminum compound is at least one trialkylaluminum compound where each alkyl group contains two or more carbon atoms.

3. The process according to claim 1 where the organoaluminum compound is at least one alkylaluminoxane where the alkyl moieties contain two or more carbon atoms.

4. The process according to any of claims 1, 2 or 3 where the alkylaluminoxane precursor is prepared by treating at least one trialkylaluminum compound with a compound containing an oxygen-carbon bond.

5. The process according to claim 4 where the modified precursor is converted to an alkylaluminoxane composition by thermolysis.

6. The process according to claim 5 where the alkylaluminoxane precursor is formed by treating trimethylaluminum with carbon dioxide.

7. A process for making a hydrocarbon-soluble alkylaluminoxane composition that comprises:

(a) preparing a modified alkylaluminoxane precursor via non-hydrolytic means; and (b) converting that modified precursor to an alkylaluminoxane, wherein the modified alkylaluminoxane precursor is formed by treating a mixture of trimethylaluminum and an organoaluminum compound, where the alkyl moieties contain two or more carbon atoms, with a compound containing an oxygen-carbon bond.

8. The process according to claim 7 where the alkylaluminoxane precursor is formed by treating trimethylaluminum and the organoaluminum compound with carbon dioxide.

9. The process according to claim 7 where the modified precursor is converted to an alkylaluminoxane composition by thermolysis.

10. The process according to claim 7 where the alkylaluminoxane precursor is formed by treating trimethylaluminum with carbon dioxide.

11. A process for making a hydrocarbon-soluble alkylaluminoxane composition that comprises:

(a) preparing a methylaluminoxane precursor via non-hydrolytic means;

(b) converting that precursor to a methylaluminoxane; and (c) treating the methylaluminoxane material with a solubilizing amount of an alkylaluminoxane wherein the alkyl moieties contain two or more carbon atoms.

12. The process according to claim 11 wherein the methylaluminoxane precursor is prepared by treating trimethylaluminum with a compound containing an oxygen-carbon bond.

13. The process according to claim 11 where the methylaluminoxane precursor is converted to methylaluminoxane by thermolysis.

14. The process according to claim 11 where the methylaluminoxane precursor is formed by treating trimethylaluminum with carbon dioxide.

15. The process according to any one of claims 1, 7 or 11 conducted in aliphatic hydrocarbon solvent.

16. The process according to any one of claims 1, 7 or 11 conducted in aromatic hydrocarbon solvent.

17. A alkylaluminoxane composition produced by any of the processes of claims 1, 7 or 11.

18. A supported alkylaluminoxane composition produced by any of the processes of claims 1, 7 or 11.

19. A silica supported alkylaluminoxane composition produced by any of the processes of claims 1, 7 or 11.

20. Alkylaluminoxane compositions produced by any of the processes of claims 1, 7 or 11 in an aliphatic hydrocarbon solvent.

21. Alkylaluminoxane compositions produced by any of the processes of claims 1, 7 or 11 in an aliphatic hydrocarbon solvent selected from the group consisting of heptane, one or more octanes, one or more decanes, and mixtures thereof.

22. A alkylaluminoxane composition produced by any of the processes of claims 1, 7 or 11 in an aromatic hydrocarbon solvent.

23. A polymerization catalyst composition which contains, as a cocatalyst component, at least one alkylaluminoxane composition produced by any of the processes of claims 1, 7 or 11.

* * * * *